(12) United States Patent
Guo et al.

(10) Patent No.: US 11,654,259 B2
(45) Date of Patent: May 23, 2023

(54) MICROCATHETER

(71) Applicant: ORBUSNEICH MEDICAL (SHENZHEN) CO., LTD., Guangdone (CN)

(72) Inventors: Lixia Guo, Guangdone (CN); Pengtao Zhang, Guangdone (CN)

(73) Assignee: ORBUSNEICH MEDICAL (SHENZHEN) CO., LTD., Guangdong (CN)

(*) Notice: Subject to any disclaimer, the term of this patent is extended or adjusted under 35 U.S.C. 154(b) by 915 days.

(21) Appl. No.: 16/485,137

(22) PCT Filed: May 3, 2018

(86) PCT No.: PCT/CN2018/085444
§ 371 (c)(1),
(2) Date: Aug. 9, 2019

(87) PCT Pub. No.: WO2019/184048
PCT Pub. Date: Oct. 3, 2019

(65) Prior Publication Data
US 2021/0213243 A1 Jul. 15, 2021

(30) Foreign Application Priority Data
Apr. 28, 2018 (CN) .......................... 201810404958.5

(51) Int. Cl.
*A61M 25/00* (2006.01)
*A61M 25/06* (2006.01)

(52) U.S. Cl.
CPC .... *A61M 25/0021* (2013.01); *A61M 25/0045* (2013.01); *A61M 25/0053* (2013.01); *A61M 25/06* (2013.01); *A61M 2025/0042* (2013.01)

(58) Field of Classification Search
CPC .......... A61M 25/0021; A61M 25/0045; A61M 25/0053; A61M 25/06; A61M 2025/0042;
(Continued)

(56) References Cited

U.S. PATENT DOCUMENTS 5,019,057 A * 5/1991 Truckai ............... A61M 25/005
87/8
5,851,203 A * 12/1998 van Muiden ..... A61M 25/0054
604/524

(Continued)

*Primary Examiner* — Theodore J Stigell
(74) *Attorney, Agent, or Firm* — Andrew F. Young; Nolte Lackenbach Siegel (57) ABSTRACT

The present invention discloses a microcatheter, with tubular structure, comprising a catheter body, a sharp portion disposed at a distal end of the catheter body, the catheter body comprises: a inner layer with a hollow lumen; a tubular intermediate layer wrapped outside the inner layer, comprising a spring layer and a braid above the spring layer, the braid extending longitudinally along a part of the spring layer; and a tubular outer layer, wrapped outside the intermediate layer; the part of the spring layer which is not wrapped by the braid is bent at a certain angle along a longitudinal axis of the catheter body. The catheter body of the microcatheter of the invention is configured to have a multilayered structure, and the braid is only wrapped on spring layer near to the proximal end; the part of the spring layer not wrapped by the braid can be bent at a corresponding angle to adapt to an angle between the main branch and the branch of the coronary artery, to make sure that the microcatheter can reach the bifurcation lesions of the coronary artery.

14 Claims, 8 Drawing Sheets

(58) Field of Classification Search
CPC .......... A61M 25/0054; A61M 25/0144; A61M 25/005; A61M 25/008; A61M 25/01; A61M 25/0662; A61M 2025/0035
See application file for complete search history.

(56) References Cited

U.S. PATENT DOCUMENTS

| | | | | |
|---|---|---|---|---|
| 9,775,963 | B2* | 10/2017 | Miller | A61M 25/0012 |
| 2003/0009095 | A1* | 1/2003 | Skarda | C22C 14/00 |
| | | | | 606/41 |
| 2010/0030191 | A1* | 2/2010 | McFerran | A61M 25/0041 |
| | | | | 604/523 |
| 2016/0346506 | A1* | 12/2016 | Jackson | A61M 25/0053 |

* cited by examiner

MICROCATHETER

CROSS-REFERENCE TO RELATED APPLICATIONS

The present application is a national phase of Ser. No. PCT/CN2018/085444 filed May 3, 2018, the entire contents of which are incorporated herein by reference, and which claims priority to and the benefit of Chinese Patent Application No. 201810404958.5 filed Apr. 28, 2018.

BACKGROUND OF THE INVENTION

1. Field of the Invention

This invention relates to the field of medical apparatus and instruments, and particularly to a microcatheter that is capable of bending to approximate a side branch.

2. Description of the Related Art

In clinic, in order to improve a success rate of a guide wire passing through blood vessels during an interventional surgery, the microcatheter is usually used in combination with the guide wire. The microcatheter can provide support to the guide wire and provide a passage for the guide wire to pass through the blood vessels.

According to the statistics of existing interventional treatment cases, it is found that bifurcation lesions are relatively more common, mainly occurring in the main branch and/or branch of the coronary artery. The branch of the coronary artery, that is, the bifurcation appearing at an end of the main branch, has a different bifurcation angle. The existing microcatheter cannot smoothly enter the branch of the coronary artery after entering the main branch of the coronary artery, which affects the guidewire, a dilatation balloon catheter or a stent system to reach the lesion site, resulting in the severe consequences of the interruption or failure of the interventional surgery.

SUMMARY OF THE INVENTION

In order to solve the above discussed technical problem in the prior art that the microcatheter can't help the guide wire to reach the bifurcation lesion of the coronary artery, which affects the normal operation of interventional operation, the invention provides an improved microcatheter with side branch access capability.

To achieve the above objectives, the present invention employs the following technical solutions:

The present invention provides a microcatheter, with tubular structure, comprising a catheter body, a sharp portion disposed at a distal end of the catheter body; wherein the catheter body has a proximal end and a distal end, the catheter body comprises:

a inner layer, with a hollow lumen;

a tubular intermediate layer wrapped outside the inner layer, comprising a spring layer and a braid above the spring layer, the braid extending longitudinally along a part of the spring layer; and a tubular outer layer, wrapped outside the intermediate layer;

wherein, the part of the spring layer which is not wrapped by the braid is bent at a certain angle along a longitudinal axis of the catheter body.

Further, a ratio of a length of the part of the spring layer which is not wrapped by the braid to the length of the part of the spring layer which is wrapped by the braid is from 1:3 to 1:10, preferably 1:5 to 1:9, more preferably 1:8.

Further, a rigidity of the intermediate layer is greater than the rigidity of the inner layer and the outer layer; the outer layer is made of thermoplastic polymer, and the thermoplastic polymer of the outer layer is embedded in the intermediate layer so as to cover the intermediate layer.

Further preferably, the spring layer is a spring tube, a hollow skeleton tube or a braided tube.

Further, an outer diameter of the spring layer decreases gradually from the proximal end of the catheter body to the distal end of the catheter body.

Further, the spring layer comprises spiral winding flat filaments.

Further, the braid comprises a plurality of winding filaments.

Further preferably, the braid comprises round filaments and flat filaments.

Further preferably, the braid extends spirally around the spring layer in a direction of the longitudinal axis of the catheter body.

Further preferably, the braid is formed by interlacing a plurality of filaments, and at least one of the filaments protrudes outwardly from other filaments so that a helical convex rib can be formed on an outer surface of the braid.

Further, the rigidity of the outer layer decreases gradually from the proximal end of the catheter body to the distal end of the catheter body.

Further, the outer diameter of the outer layer decreases gradually from the proximal end of the catheter body to the distal end of the catheter body.

Further, the thickness of a wall of the outer layer decreases gradually from the proximal end of the catheter body to the distal end of the catheter body.

Further, the spring layer is a tapered spring whose diameter decreases gradually from the proximal end to the distal end of the catheter body, and the spring layer comprises a distal section, a proximal section, a gradational section connected between the distal section and the proximal section, and wherein a pitch of the distal section and the proximal section is constant, and the pitch of the distal section is greater than the pitch of the proximal section, and the pitch of the gradational section tends to increase in a direction from the proximal end to the distal end.

Further, the pitch of the distal section is 180 PPI, the pitch of the proximal section is 80 PPI, and the pitch of the gradational section gradually transfers from 80 PPI to 180 PPI from the proximal end to the distal end.

Further, the outer layer is a spiral corrugated tube, which comprises: a spirally convex wave crest and a concave wave trough relative to the wave crest on the outer surface of the spiral corrugated tube, and wherein the part of the spring layer which is not wrapped by the braid is a spring tube, and the wave trough of the outer layer is embedded in a gap between threads of the spring tube, the wave crest of the outer layer and the threads of the spring tube are in contact and bonded together.

Further, the thickness of the wall of the spiral corrugated tube tends to decrease from the proximal end to the distal end along the direction of the longitudinal axis of the catheter body, and a distance between two adjacent wave crests tends to increase from the proximal end to the distal end along the direction of the longitudinal axis of the catheter body.

Further, the outer diameter of the catheter body decreases gradually from 2.8 F-2.5 F to 2.1 F-1.9 F from the proximal end to the distal end, the rigidity of the catheter body transfers gradually from 120 gf-70 gf to 5 gf-2 gf from the proximal end to the distal end.

Further, the part of the spring layer which is not wrapped by the braid is provided at a position at a distance of 10 mm-60 mm from a tip of the sharp portion.

Further, the microcatheter further comprises:
a needle base, arranged proximal to the catheter body; and
a connecting member, located between the needle base and the catheter body, the rigidity of which is smaller than that of the catheter body.

Further, at least one of the spring layer and the braid is made of stainless steel or nickel-titanium alloy.

Further, the part of the spring layer which is not wrapped by the braid is bent at a certain angle, such that the sharp portion of the distal end of the catheter body can be guided into an entrance of a side branch artery.

Further preferably, the microcatheter further comprises:
a guide wire, arranged in a lumen of the catheter body, extending through the spring layer;
wherein by retracting the guide wire from the distal end of the spring layer, the part of the spring layer not wrapped by the braid is bent at a certain angle relative to the longitudinal axis of the catheter body, so that the sharp portion of the distal end of the catheter body can be guided into the entrance of the side branch artery.

Further, the portion of the spring layer which is not wrapped by the braiding can be bent within a range of about 25° to about 140° with respect to the longitudinal axis of the catheter body.

By employing the above technical solutions, the present invention has the following technical effects compared with the prior art:

The catheter body of the microcatheter of the present invention is provided as a multilayer structure, and the braid is only wrapped around the proximal end, near the outer wall of the spring layer; the part of the spring layer not wrapped by the braid can be bent at a corresponding angle to adjust to the angle between the main branch and the branch of the coronary artery, to make sure that the microcatheter can reach the bifurcation lesions of the coronary artery; besides, the rigidity of a pushing section of the catheter body is greater than the rigidity of a shaping section of the catheter body, thereby, the pushing section of the catheter body can provide a certain support force and a recoil force at the proximal end of the shaping section to improve the torque control force of the microcatheter, so that the catheter body has enough torsional pushing force and supporting force to improve the traversing, traceability and flexibility of the microcatheter effectively.

BRIEF DESCRIPTION OF THE DRAWINGS

The accompanying drawings, together with the specification, illustrate exemplary embodiments of the present disclosure, and, together with the description, serve to explain the principles of the present invention.

DETAILED DESCRIPTION

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "plurality" means a number greater than one. And the direction term "proximal" is defined as a direction close to the operator during the operation, "distal" is defined as the direction away from the operator during the operation.

Hereinafter, certain exemplary embodiments according to the present disclosure will be described with reference to the accompanying drawings.

Figure 1:
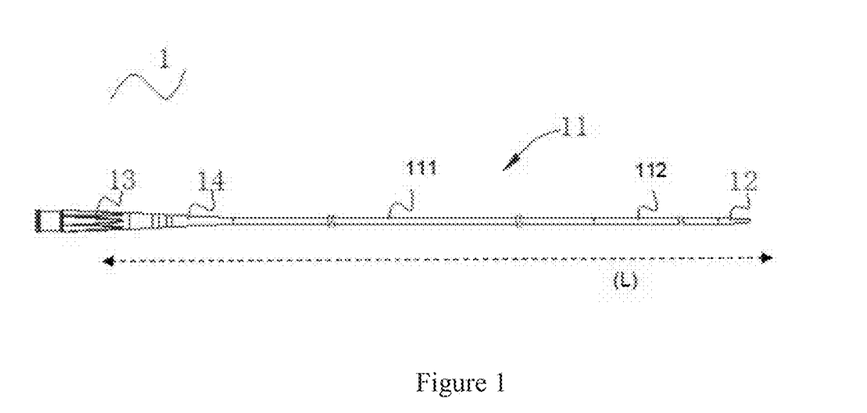
FIG. 1 is a schematic view of the microcatheter according to the present invention.

As shown in FIG. 1, the embodiment of the present invention provides a tubular structure of a microcatheter 1, comprising a catheter body 11 and a sharp portion 12 disposed at a distal end of the catheter body 11. The catheter body 11 extends longitudinally along an axis L, and herein the axis L is referred to as a longitudinal axis of the catheter body 11. The sharp portion 12 may be made of a mixture of tungsten powder (70%) and a thermoplastic elastomer material, and may have sufficient softness and flexibility to prevent damage to a lining of the blood vessel with which it is in contact.

The catheter body 11 has a pushing section 111 at its proximal end and a shaping section 112 at its distal end along the longitudinal axis L thereof. The shaping section 112 can be pre-shaped by bending without bending deformation under a suitable external force, and can maintain the preformed shape after the external force is removed, so that a portion of the shaping section 112 can be shaped at a certain angle along the longitudinal axis L of the catheter body 11, and the shaped microcatheter 1 can generate better supporting force for helping the guide wire enter a severely tortuous or calcified lesions smoothly.

Meanwhile, the rigidity of the pushing section 111 is greater than that of the shaping section 112, thus, the pushing section 111 can provide a certain supporting force and recoil force near to the shaping section 112 to improve the torque control force of the microcatheter 1 and provide the catheter body 11 sufficient torsional pushing force and supporting force, so that the traversing, traceability and flexibility of the microcatheter 1 can be improved effectively.

Moreover, the microcatheter 1 further comprises a needle base 13, which is arranged at the proximal end of the catheter body 11. The needle base 13, for example, may be made of polycarbonate, polyester, polyamide and polyimide, and can be adapted to be bonded to a standard luer connector. A connecting member 14 is provided between the needle base 13 and the catheter body 11. The connecting member 14 may be made of an elastomeric material having a rigidity (but the rigidity is lower than the rigidity of the catheter body 11) to cause a soft/hard transition between the needle base 13 and the catheter body 11.

The operator usually controls the microcatheter by rotating the connecting member 14 during the operation. In the embodiment of the present invention, based on the A Type Shore Hardness Tester, the rigidity of the connecting member 14 may be from 15 A to 75 A, from 25 A to 65 A or from 35 A to 55 A to facilitate the operator's operation. The Shore Hardness Tester adapted is recorded in the American Society for Testing and Materials (ASTM) Standard D-2240. The ASTMD-2240 Hardness Tester applies a predetermined amount of force to a sample in a consistent manner and measures the rigidity based on a depth of an indentation caused by the applied force. According to the "A" type test set by a scale, a hardened steel bar with a diameter of 1.1 mm to 1.4 mm and a truncated cone with a cone angle of 35° are applied to make the indentation.

Figure 2:
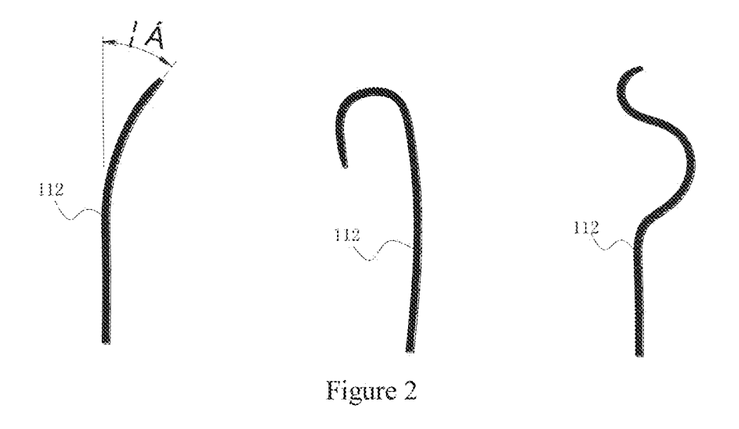
FIG. 2 is a schematic view of the use of the microcatheter according to the present invention.

As shown in FIG. 2, in the actual application, the doctor can use a puncture needle to make a part of the shaping section 112 to bend at a certain angle along the longitudinal axis L of the catheter body 11 according to the actual demand. For example, the bending angle α of the shaping section 112 may be similar to the angle of a starting section of the blood vessel, wherein α may range from about 250 to about 140°, about 30 to about 130°, about 40° to about 120°, about 50° to about 110°, about 30° to about 100°, about 30° to about 90°, about 50° to about 110°, about 25°, about 30°, about 40°, about 50°, about 60°, about 70°, about 80°, about 90°, about 100°, about 110°, about 120° or about 130°. Besides, depending on an anatomy requirement of a specific size of a branch entrance, the shaping section 112 can also be directly bent into a J-shaped elbow whose bend radius should not be greater than the diameter of the blood vessel; the shaping section 112 can also be bent into S-shaped or semi-circular shape. Generally, the shaping section 112 may be formed in a variety of curved shapes, including flat, simple curves, complex curves, reverse curves or hyperbolas. A length of the curved section may vary and may include different lengths of the shaped section. The force can be applied in a variety ways, such as through the guide wire that can be inserted into the lumen of the inner layer.

Based on clinical needs, in some embodiments, the shaping section 112 may be shaped to have a varying bend radius to form a multi-level elbow. When the curvature of the shaping section 112 deviates from a desired requirement, the shaping section 112 can be restored to its original shape by a suitable external force, for example by application of heat, then followed by a secondary shaping.

In some embodiments, the shaping section 112 of the catheter body 11 is disposed at a distance of about 10 mm to about 60 mm from the end of the sharp portion 12 to achieve improved side branch access. Because of the flexibility and bendability of the shaping section 112, the microcatheter can access a distal vasculature by manipulating the guide wire. Moreover, the microcatheter 1 can pass through the injury site and deliver the guide wire and/or a contrast agent through the site of the injury, for example by deploying an interventional treatment element at the site of the injury and then immediately restore blood flow.

In addition, the shaping section 112 enters the side branch of the vasculature. When the microcatheter within the aorta reaches a branch point where the side branch is detached from the aorta, the shaping section 112 can be bent at an appropriate angle (e.g., about 300 to about 140°) with respect to the longitudinal axis L of the catheter body 11 to point to the entry of the side branch, for example, by removing the guide wire from the microcatheter. When the microcatheter is manipulated by the operator, the shaping section 112 having been directed to the entrance of the side branch can be moved into the side branch artery through the entrance. It should be noted that the torque force can be applied to the catheter by rotating the needle base of the catheter body that is rotatable about a central axis.

In the present embodiment, a ratio of the softness of the shaping section 112 to the cubic diameter of the shaping section 112 is 9 gf-17 gf/inch$^3$. The material of the intermediate layer 1122 of the shaping section is metal, its rigidity is greater than those of the inner layer 1121 and the outer layer 1123 of the shaping section. The intermediate section 1122 of the shaping layer having a relatively high rigidity provides enough rigidity for the shaping section 112, and the inner layer 1121 and the outer layer 1123 of the shaping section having a lower rigidity provide a corresponding flexibility for the shaping section 112, thereby enabling the rigidity and the flexibility of the shaping section 112 to coexist, and thus the deformation can be memorized while being deformed.

Figure 3:
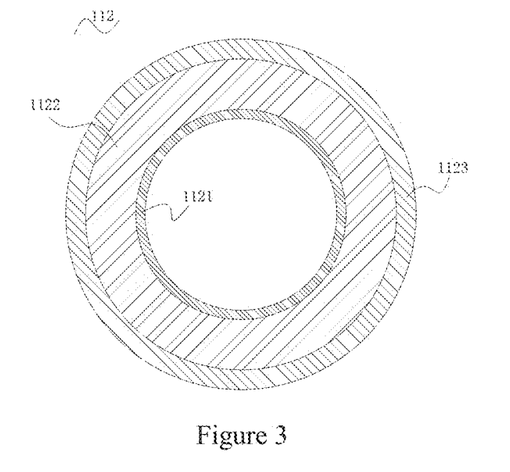
FIG. 3 is a schematic sectional view of the shaping section in the microcatheter according to the present invention.

Referring to FIG. 3, a schematic cross-sectional view of the shaping section 112 of the catheter body is shown. The shaping section 112 of the catheter body 11 in the present embodiment is a concentric three-layer structure, which comprises: a inner layer 1121 of the shaping section with a hollow lumen; a tubular intermediate layer 1122 of the shaping section wrapped outside the inner layer 1121 of the shaping section, wherein the intermediate layer 1122 of the shaping section is a spring layer not wrap with the braid; and a tubular outer layer 1123 of the shaping section wrapped outside the intermediate layer 1122 of the shaping section, a part of the intermediate layer 1122 of the shaping section not wrapped with the braid is bent at a certain angle along the longitudinal axis L of the catheter body 11. Thereby, when the microcatheter 1 needs to pass through a branch lesion in the coronary artery, the shaping section 112 can be previously bent at a corresponding angle in vitro to adapt the angle between the branch and the main branch of the coronary artery, so that the microcatheter 1 can pass through the branch lesions smoothly. In the inner layer 1121 of the shaping section of the catheter body 11, a desired material is interposed, such as a drug, a guide wire may be provided in the hollow lumen of the inner layer 1121 of the shaping section. The outer diameter of the distal end of the catheter body 11 can also vary as measured at the outer surface of the outer layer 1123 of the shaping section, for example from about 0.2 mm to about 2 mm, for example about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm and so on.

In the present embodiment, the intermediate layer of the catheter body 11 is made of a metal material, and the rigidity of the intermediate layer 1112 of the pushing section is greater than the rigidity of the intermediate layer 1122 of the shaping section. The inner layer 1111 of the pushing section 111 is integrated with the inner layer 1121 of the shaping layer 112 to form the inner layer of the catheter body 11, and the outer layer 1113 of the pushing section 111 is integrated with the outer layer 1123 of the shaping section 112 to form the catheter layer of the catheter body 11.

With continued reference to FIG. 3, in the present embodiment, the wall of the intermediate layer 1122 of the shaping section has a plurality of voids. The outer layer 1123 is embedded in the void of the intermediate layer 1122 of the shaping section and is heat-fused with the inner layer 1121 so that the shaping section 112 becomes an integrated structure from inside to outside, and the integrated structure is softer and has a certain degree of toughness in the void of the intermediate layer 1122, which is conductive to bending for shaping and is not easily broken, and has a certain rigidity in the intermediate layer 1122 without the voids, which is conductive to maintaining the shape after being shaped. Besides, since the outer layer 1123 is embedded in the void of the intermediate layer 1122 and is heat-fused with the inner layer 1121, so that the catheter body 11 forms a self-locking structure similar to the lead angle of the thread at the void of the intermediate layer 1122 so that a memory microcatheter 1 with a better preformed effect is obtained.

In the present embodiment, the intermediate layer 1122 of the shaping section 112 is a spring tube, the void is formed between the adjacent threads of the spring tube, wherein the outer layer 1123 of the shaping section is embedded in the void of the adjacent threads and is bonded with inner layer 1121 of the shaping section so as to obtain a better preformed ability.

The outer layer 1123 may be made of a material with good flowability, the inner layer 1121 may be made of a material with poor flowability, wherein the outer layer 1123 herein is made of a thermoplastic polymer, and the thermoplastic polymer of the outer layer 1123 of the shaping section is embedded in the intermediate layer 1122 of the shaping section to wrap around the intermediate layer 1122 of the shaping section. When the outer layer and the inner layer are hot-melt-bonded, the outer layer 1123 of the shaping section can penetrate and diffuse into the inner layer 1121 of the shaping section through the void of the intermediate layer 1122 of the shaping section to achieve melting.

Figure 4:
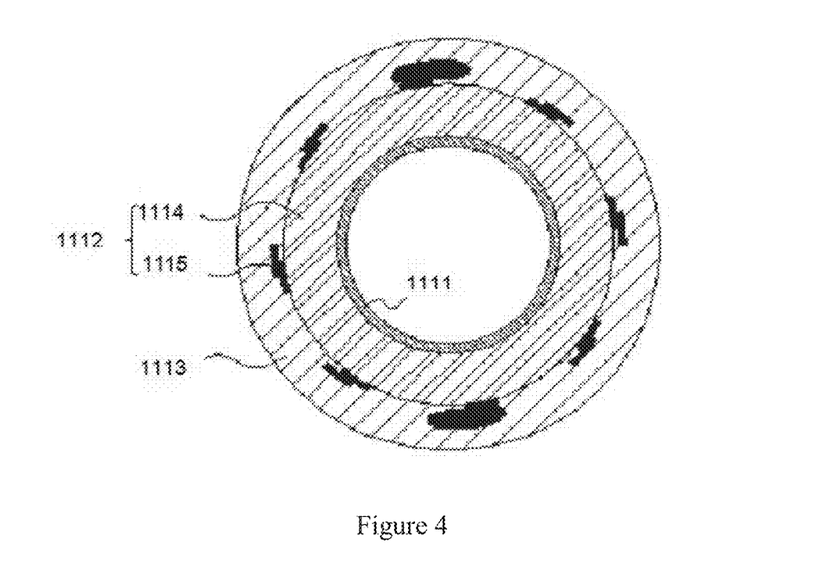
FIG. 4 is a schematic sectional view of the pushing section in the microcatheter according to the present invention.

Referring to FIG. 4, a schematic cross-sectional view of the position of the pushing section 111 that the spring layer 1124 is wrapped with the braid 1115 in the microcatheter is shown. The pushing section 111 of the present embodiment includes, from the inner to the outer, a inner layer 1111 of the pushing section having a hollow lumen, a tubular intermediate layer 1113 of the pushing section wrapped outside the inner layer 1111 of the pushing section, and a tubular outer layer 1113 of the pushing section wrapped outside the intermediate layer 1112 of the pushing section. Wherein, the intermediate layer 1112 of the pushing section is made of a metal material, and the rigidity of the intermediate layer 1112 of the pushing section is greater than the rigidity of the intermediate layer 1122 of the shaping section.

Figure 5:
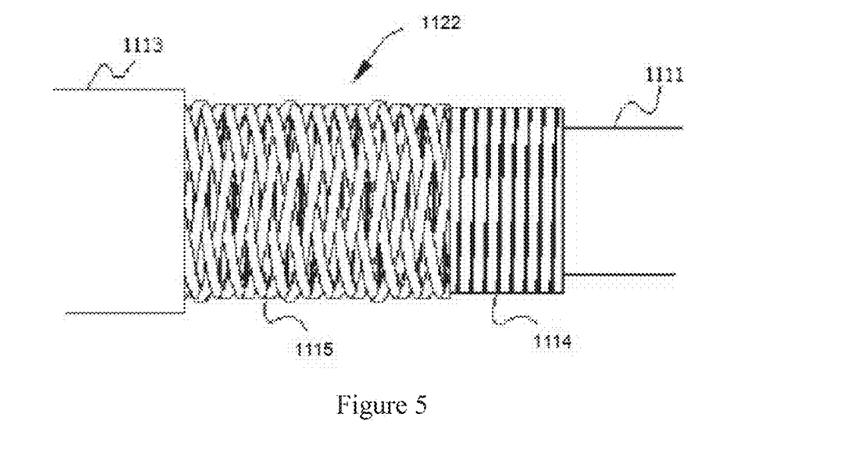
FIG. 5 is a schematic view of the pushing section in the microcatheter according to the present invention.

The FIG. 5 is shown as a longitudinal side view of the catheter body 11, the intermediate layer 1112 of the shaping section is a double-layered tube comprising a spring layer 1114 and a braid 1115 wrapping around a longitudinal part of the spring layer 1114 from the proximal end. The intermediate layer of the catheter body 11 is formed integrally by the intermediate layer 1112 of the shaping section extending to the pushing section 111, and the braid 1115 is wrapped outside the spring layer 1114. In some embodiment, the braid 1115 wrapped around about 10%-95%, about 30%-80%, about 40%-70%, about 60%-90%, or about 75%-87.5% of the entire longitudinal length of the spring layer 1114. A bending point is located at the distal end of the position where the braid 1115 wrapping range ends. However, the bending point may occur at any point along the shaping section 112. In a particular embodiment, the braid 1115 may wrap around 87.5% of the entire spring layer 1114, for example, the length of the spring layer 1124 is 1.35 m, then the length of the braid 1115 is 1.2 m, thereby, 0.15 m of spring layer 1114 is not wrapped with the braid 1115.

The outer surface of the spring layer 1124 of the shaping section is not completely wrapped with the braid 1115 (partial) as shown in FIG. 5, the part of the microcatheter with a extending braid 1115 has an extra rigidity and elasticity compared to the portion without the braid 1115 so that the portion containing the braid 1115 constitutes the pushing section 111 of the catheter body 11; the portion not containing the braid 1115 constitutes the shaping section 112 of the catheter body 11. When the microcatheter enters the blood vessel, a stiffer pushing section can be used to provide forward thrust to advance the microcatheter through an obstacle such as a severe lesion.

In the present embodiment, the outer diameter of the entire spring layer of the catheter body 11 which consists of the spring layer 1114 of the pushing section and the spring layer 1124 of the shaping section decreases from the proximal end to the distal end. The spring layer may comprise a winding flat filaments made of stainless steel or Nitinol. It can also be made of other metal materials. For example, other metals include superelastic nickel titanium, shape memory nickel titanium, Ti—Ni, nickel titanium, approximately 55-60 wt % of Ni, Ni—Ti—Hf, Ni—Ti—Pd, Ni—Mn—Ga, 300 to 400 series of SAE grade stainless steel (SST), such as 304, 316, 402, 440, MP35N and 17-7 precipitation hardening (PH) stainless steel, other spring steels, other high tensile strength materials or other biocompatible metal materials. In a preferred embodiment, the material is superelastic or shape memory nickel titanium; in another preferred embodiment, the material is stainless steel.

The spring layer may include a superelastic alloy normally called "shape memory alloy". Components made of this shape memory alloy have the ability to recover their original shapes after deformation, so that they will undergo permanent deformation if they are made of ordinary metals. The superelastic alloys used in the present invention include: Elgiloy® and Phynox® spring alloys (Elgiloy® alloys are available from Carpenter Technology Corporation, Reading Pa.; Phynox® alloys are available from Metal Imphy, Imphy, France), SAE grade 316 stainless steels, MP35N (nickel-cobalt) alloys obtained from Carpenter Technology, Latrobe Steel, Latrobe, Pa., and superelastic Nitinol, available from Shape Memory Applications, Santa Clara, Calif. Further information on one or more of these alloys is disclosed in the U.S. Pat. No. 5,891,191.

As described above, suitable superelastic alloys include nickel titanium (Nitinol) consisting essentially of 49-53 atomic percent Ni, Cu—Zn alloy consisting essentially of 38.5-41.5 wt % Zn, Cu—Zn—X alloy containing 1-10 wt % X (X=Be, Si, Sn, Al or Ga), and Ni—Al alloy consisting essentially of 36-38 atomic percent Al. The particularly preferred superelastic alloy is Nitinol. The mechanical property of the nickel-titanium alloy can be changed as needed, replacing a part of the Ti—Ni alloy with another element X (X=Cu, Pd or Zr) of 0.01 to 30.0 atomic percent, or selecting the condition for cold processing and/or final heat treatment. The bending strength (stress generated when the load is increased) of the superelastic alloy used is 5-200 kg/mm$^2$ (22° C.), preferably 8-150 kg/mm$^2$, and the recovery stress (stress generated when the load is reduced) is 3-180 kg/mm$^2$ (22° C.), preferably 5-130 kg/mm$^2$. Alternatively, the spring layer may be formed from a polymer. Examples of polymers include polymide, PEEK, nylon, polyurethane, polyethylene terephthalate (PET), latex, HDHMWPE (high density, high molecular weight polyethylene) and thermoplastic elastomers.

For example, the spring layer can be prepared by forming a superelastic metal tube, and then by removing the portion of the tube that will form recesses or holes. The recesses, holes or cuts may be formed in the pipe by the way that may be selected from the group of consisting of laser (e.g., YAG laser), electrical discharge, chemical etching, mechanical cutting or a combination thereof. U.S. Pat. No. 5,879,381, inventor Moriuchi et al., is incorporated by reference in its entirety herein.

After being deformed and deformed into a predetermined shape (for example, a curved shape) by heating, the spring layer may be cooled. The spring layer is then constrained in a deformed state within a delivery system to facilitate insertion into blood vessels such as arteries. Once the physical constraints on the tubular module have been removed, the superelastic tubular module can returned to its original underformed shape, i.e. curve.

In one embodiment, the spring layer may be formed of a plurality of spiral portions. The spring layer may have several different types of spiral cutting patterns, comprising continuous and discontinuous spiral cutting patterns. The different spiral cutting patterns may be distributed on the same or different tubular modules. The spiral cutting section can provide a gradual transition of bending flexibility by pushability, kink resistance, axial torque transmission for rotational response and/or torque on fault measurement. For example, the spiral cutting patterns may have a varying pitch to increase flexibility in one or more regions of the spring layer. The spiral cutting pitch can be measured by the distance between points in the same radial position in two adjacent threads. In one embodiment, the pitch may increase when the spiral cutting progresses from the proximal position to the distal position of the catheter. By adjusting the pitch and the incision and the uncut path of the spiral incision, the pushability, kink resistance, torque, flexibility, and compression resistance of the catheter (i.e. the tubular module) can be adjusted.

In addition, when the tubular module is bent or tortuous, the spiral cutting pattern allows to maintain the cross-sectional diameter of the lumen. The spiral cutting sections with different cutting patterns may be distributed along the length of the tubular module. The spiral pattern may be continuous or discontinuous along the length of the module. For example, there may be 1, 2, 3, 4, 5, 6, 7, . . . n spiral cutting sections along the length of the module. The spiral cutting sections may be continuous or discontinuous. There may be a constant cutting pattern within each section, but the cutting pattern can be changed for example according to the pitch in the different sections of the tubular module. Each section can also contain a variable pitch pattern within a specific section. Each spiral cutting section may have a constant pitch, for example in the range of about 0.05 mm to about 10 mm, for example 0.1 mm, 0.2 mm, 0.3 mm, 0.4 mm, 0.5 mm, 0.6 mm, 0.7 mm, 0.8 mm, 0.9 mm, 1.0 mm, 1.5 mm, 2.0 mm and so on. The pitch can also vary within each section. The pitch of the different spiral cutting sections may be the same or different. Alternatively, the catheter may be formed of a tubular module having a continuously varying spiral cutting pattern along the length of the catheter. The orientation in the module or the helicity of the spiral cutting section may also vary within the spiral incision. The width of the spiral incision can vary, for example from about 1 micro to about 100 microns. In another embodiment, the spring layer may be a continuous coil.

The braid 1115 of the intermediate layer 1112 of the pushing section is formed by alternatively interlacing a plurality of strands of filaments. At least one strand of the filaments protrudes outwardly from other threads so that the outer surface of the braid 1115 has convex ribs with streamline. The braiding density of the braid 1115 in the present embodiment gradually changed from 60 PPI to 160 PPI from the proximal end to the distal end.

Figure 6:
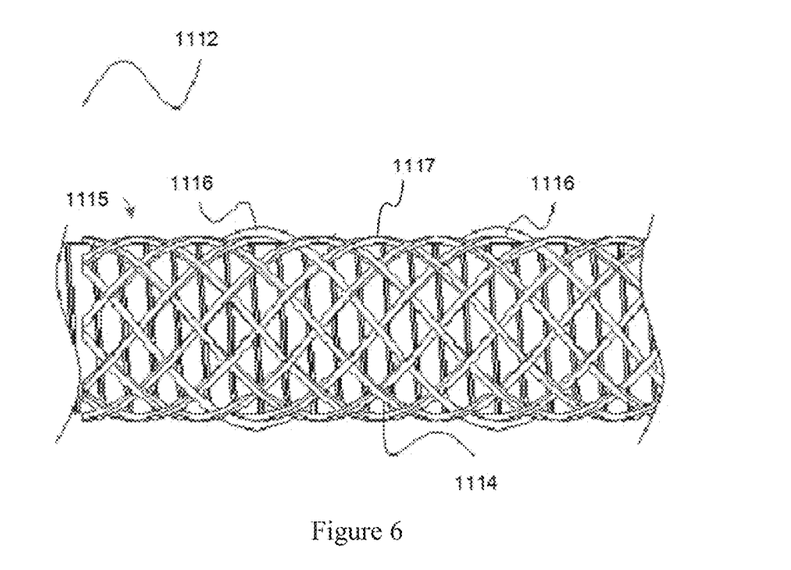
FIG. 6 is a schematic view of the intermediate layer of the pushing section of the pushing section in the microcatheter according to the present invention.

Preferably, as shown in FIG. 6, in the present embodiment, the braid 1115 is formed by alternatively interlacing thick threads 1116 and thin threads 1117. The surface of the thick thread 1116 protrudes outwardly from the surface of the thin thread 1117, and the protruding thick thread 1116 extends spirally along the axial direction of the braid. In the microcatheter 1 provided in such a configuration, the thick thread 1116 can form a spiral protrusion on the surface of the outer layer after the outer layer of the catheter body 11 is wrapped around the braid 1115, so that the contact area between the microcatheter 1 and the inner wall of the blood vessel is reduced, thus the resistance of the microcatheter 1 is reduced during the pushing process.

Specifically, the braid 1115 in the present embodiment can be braided in a 1:1 or 2:2 weaving manner using 16-strand, 24-strand or 32-strand threads. When the 16-strand threads are used for weaving, 2-strand thick threads 1116 can be matched with 6-strand thin threads, followed by alternately weaving with 8-strand threads. Therein, the outer diameter of the thick thread 1116 is larger than the outer diameter of the thin thread 1117.

Figure 7:
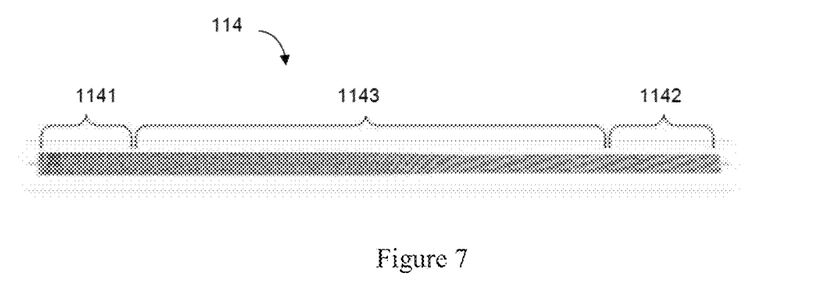
FIG. 7 is a schematic view of the spring layer of the catheter body in the microcatheter according to the present invention.

Referring to FIG. 7, in another embodiment, the spring layer 114 is a tapered spring having a diameter that tapers from the proximal end to the distal end of the catheter body 11, and the spring layer 114 may be formed by a continuous winding spring coil. The spring layer 114 comprises a distal section 1142, a proximal section 1141, and gradational section 1143 between the distal section 1142 and the proximal section 1141. In the present embodiment, the pitch of windings in the distal section and the pitch of the proximal section are constant, and the coil pitch of the distal section 1142 is greater than the coil pitch of the proximal section 1141. In the illustrated embodiment, the coil pitch of the gradational section 1143 is not constant but increases along its longitudinal length. By varying the pitch of the coils, the spring layer 114 of the catheter body 11 can increase flexibility gradually toward the distal end while maintaining proper torsional forces and malleability to enable manipulation of the microcatheter.

In the present embodiment, the pitch of the distal section 1142 and the pitch of the proximal section 1141 are both constant, and the pitch of the distal section 1142 is greater than the pitch of the proximal section 1141. Specifically, the pitch of the distal section 1142 is 180 PPI, and the pitch of the proximal section 1141 is 80 PPI; the pitch of the gradational section 1143 shows an increase trend from the proximal end to the distal end, and the pitch of the gradational section 1143 changes gradually from 80 PPI to 180 PPI from the proximal end to the distal end, thereby obtaining a better bending and shape-locking effect in the shaping section, while improving the supporting force and the recoil force of the proximal end.

In addition, the intermediate layer of the catheter body 11 in the present embodiment is a tapered spring with a diameter gradually reduced from the proximal end to the distal end to further ensure the flexibility of the distal end of the microcatheter 1.

Figure 8:
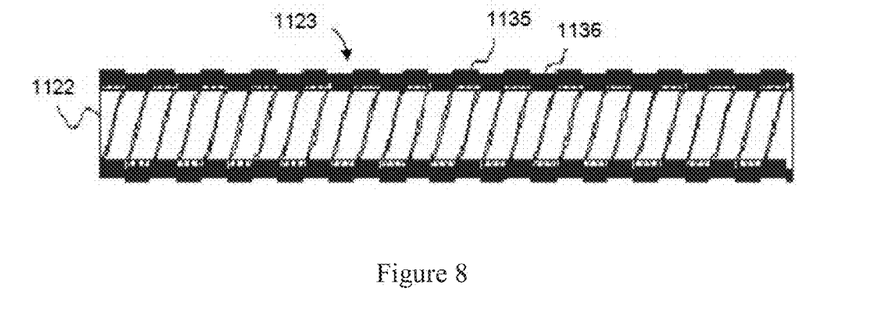
FIG. 8 is a schematic view of the outer layer of the catheter body in the microcatheter according to the present invention.

Referring to FIG. 8, in the present embodiment, the outer layer 1123 of the catheter body 11 is an integrated spiral corrugated tube, which comprises: a spirally convex wave crest 1135 and a concave wave trough 1136 relative to the wave crest on the outer surface of the spiral corrugated tube. In the present embodiment, the intermediate layer 1122 of the shaping section 112 is a spring layer. Further, the wave trough 1136 on the outer layer of the catheter body 11 is embedded in a gap between threads of the spring tube, the wave crest of the outer layer and the threads of the spring tube are in contact and bonded together. The microcatheter 1 arranged in such a configuration may form a spirally convex wavy surface on the outer surface of the catheter body 11. Since the protruding wave crest 1135 tends to contact with an inner wall of the blood vessel, and the wave trough 1136 tends not to contact with the inner wall of the blood vessel, the contact area between the outer surface of the microcatheter and the inner wall of the vessel through which the microcatheter penetrates is reduced, thereby, the friction to the blood vessel during the progress of the microcatheter advancement is reduced.

Preferably, the wall thickness of the spiral corrugated tube decreases along the direction from the proximal end to the distal end, and a distance between two adjacent wave crests 1135 increases along the direction from the proximal end to the distal end. In the present embodiment, the pitch of the spiral corrugated tube gradually changes from 80 PPI to 180 PPI from the proximal end to the distal end.

Besides, in the present embodiment, the outer diameter of the outer layer of the catheter body 11 tends to decrease along the direction from the proximal end to the distal end, and the rigidity of the outer layer of the catheter body 11 tends to decrease along the direction from the proximal end to the distal end, and the wall thickness of the outer layer of the catheter body 11 tends to decrease along the direction from the proximal end to the distal end.

Specifically, the outer layer of the catheter body 11 of the present embodiment is wrapped outside the outer surface of the intermediate layer, this outer layer may be made of only one of thermoplastic materials such as polyester, polyamide, polyimide, polyethylene, polypropylene and the like, or is formed by polymerization of the above two or more materials to obtain better lubricity and fluidity after heating of the outer layer, and improve the hot melting adhesion effect of the inner and outer layer of the catheter body 11. Preferably, the rigidity of the outer layer decrease from the proximal end to the distal end. Preferably, on a Type A Shore Hardness Scale, the rigidity of the outer layer can be within the range from about 30 A to about 80 A, about 40 A to about 70 A or about 45 A to about 65 A. In addition, the outer diameter of the outer layer 1123 can be reduced from the proximal end to distal end, which further ensures the rigidity of the catheter body 11 decreasing toward the distal end.

Figure 9:
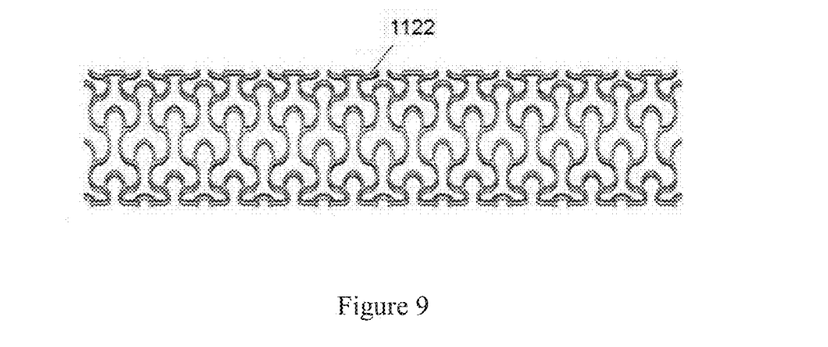
FIG. 9 is a schematic view of the intermediate layer of the shaping section in the microcatheter according to the present invention.

Referring to FIG. 9, a schematic diagram of a preferred structure of the intermediate layer of the catheter body 11 is shown, a hollowed-out skeleton tube, rather than the spring tube, is used as the intermediate layer 1122 of the shaping section, wherein the hollow in the skeleton tube forms the gap of the intermediate layer, and the outer layer of the catheter body 11 is embedded in the intermediate layer 1122 of the shaping section through the hollow in the skeleton tube and is thermally fused with the inner layer 1121 of the shaping section, so that the hollow part forms a soft and flexible structure, which is conducive to bending and is not easily broken, and the non-hollowed part has a certain rigidity, which facilitates shape retention after shaping, so that the whole microcatheter 1 is formed into a rigid and flexible intertwined structure, and thus a microcatheter 1 with a better preshaping effect and a better locking function is obtained.

Figure 10:
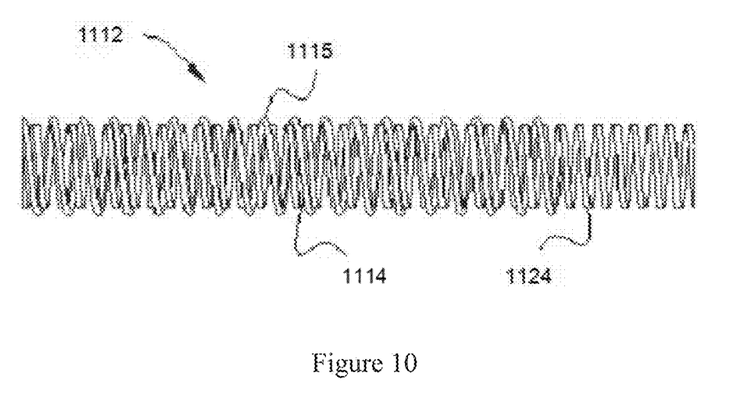
FIG. 10 is a schematic view of the intermediate layer of the pushing section in the microcatheter according to the present invention.

Referring to FIG. 10, which is another alternative embodiment of the intermediate layer of the pushing section of the catheter body 11, the intermediate layer 1112 of the pushing section comprises a spring layer 1114 and a braid 1115. This braid 1115 is a spring-like structure wound by monofilaments, and is wound around a majority of the spring layer 1114 with a relatively small pitch. The spring layer 1114 is a spring tube. The spring layer 1124 of the shaping section is not wrapped by the braid 1115 at the distal side of the spring layer 1114, namely, the intermediate layer 1112 of the pushing section is a spring-like double-layer spring structure formed by wrapping a monofilament braid around the spring tube to make sure that the ratio between the rigidity of the pushing section 111 to the rigidity of the shaping section 112 is moderate, further, the torsional force and flexion resistance in the proximal end of the microcatheter 1 is balanced, and the traversing, traceability and flexibility and supporting force in the distal end are balanced, to ensure the microcatheter 1 will reach the lesion site smoothly.

Figure 11:
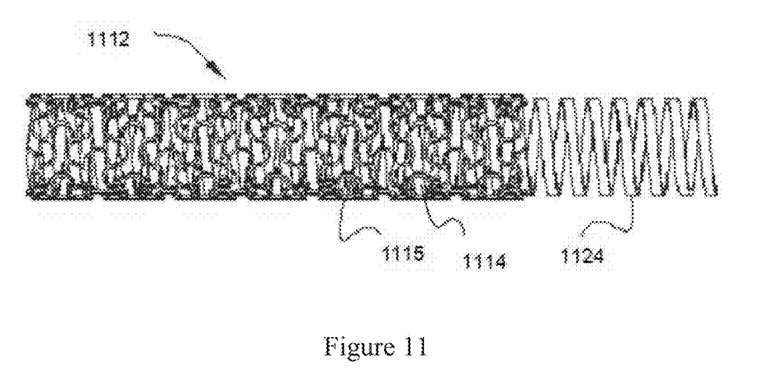
FIG. 11 is a schematic view of the intermediate layer of the pushing section in the microcatheter according to the present invention.

Referring to FIG. 11, the intermediate layer 1112 of the pushing section of the catheter body 11 comprises a spring layer 1114 and a braid 1115 partially wrapped on the spring layer 1114, wherein this spring layer 1114 is a spring tube, and the braid 1115 is a skeleton layer, the skeleton layer of the present embodiment is a hollow body structure. The skeleton layer is wrapped outside the spring tube, and the skeleton layer and the spring tube wrapped with the skeleton layer constitute the intermediate layer 1112 of the pushing section, namely, the intermediate layer 1112 of the pushing section is a structure in the form of the spring tube being sleeved on the skeleton tube, further, the torsional force and flexion resistance in the proximal end of the microcatheter 1 is balanced, and the traversing, traceability and flexibility and supporting force in the distal end are balanced, to ensure the microcatheter 1 will reach the lesion site smoothly.

Figure 12:
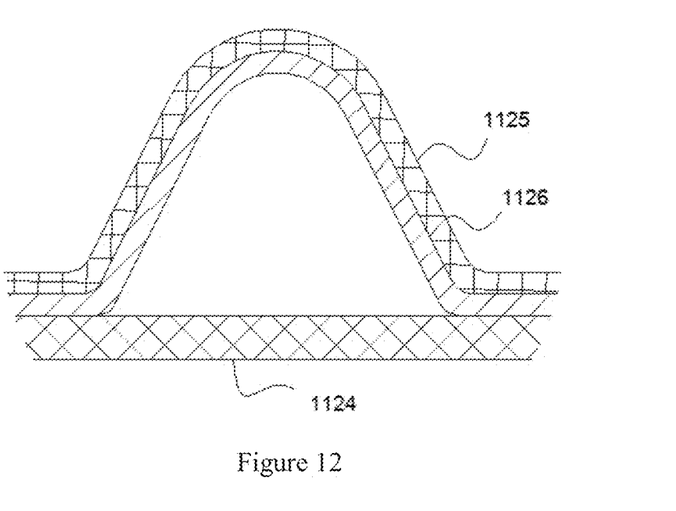
FIG. 12 is a cross-sectional view of the shaping section in the microcatheter according to the present invention.

In FIG. 12, another alternative embodiment is shown. In the present embodiment, the shaping section 112 of the microcatheter 1 comprises a spiral corrugated tube formed by a strengthening rib 1126 that is protruded periodically. The spiral corrugated tube comprises a tubular inner wall 1124 and corrugations 1125 spirally projected on an outer periphery of the inner wall, wherein the metal strengthening rib 1126 is provided on the spiral corrugated tube. The strengthening rib 1126 of this embodiment is provided between the corrugations 1125 and the inner wall 1124, fitting inside the corrugations 1125 along the corrugations 1125. In some other preferred embodiments, the strengthening rib 1126 may also be embedded in the corrugations 1125, specifically, the corrugation 1125 has a two-layer structure, and the strengthening ribs 1126 are embedded between two corrugations 1125.

A position between the adjacent corrugations 1125 of the spiral corrugated pipe is relatively soft and has a certain toughness, which is conducive to bending and is not easy to be broken, while the position of the corrugations 1125 has a certain rigidity, which is conducive to shape retention and shape locking after shaping. Accordingly, the deformation of the spiral corrugated tube after being deformed can be memorized, so as to ensure that the microcatheter 1 can adapt to different angles between the branch and the main branch of the coronary artery, and thus to make sure that the microcatheter 1 can smoothly pass through the branch lesions.

Preferably, the inner wall 1124 of the spiral corrugated tube in this embodiment may be made of a material with a small friction coefficient, so that medicine, the guide wire or other interventional systems entering the spiral corrugated tube will obtain a smaller friction force to reach the lesion site in the blood vessels smoothly.

Preferably, the outer diameter of the catheter body 11 in this embodiment decreases gradually along the direction from the proximal end to the distal end. Specifically, the outer diameter of the catheter body 11 decreases from 2.8 F-2.5 F to 2.1 F-1.9 F along the direction from the proximal end to the distal end, and the rigidity of the catheter body 11 transfers gradually from 120 gf-70 gf to 5 gf-2 gf from the proximal end to the distal end, so as to further ensure the softness of the catheter body 11 increases gradually from the proximal end to the distal end.

In this embodiment, the inner layer of the catheter body 11 is made of a material with a low coefficient of friction, such as a polymer material of nylon, polyether block amide, PTFE (polytetrafluoroethylene), FEP (fluorinated ethylene propylene), PFA (Perfluoroalkoxyalkane), PET (polyethylene terephthalate) or PEEK (polyetheretherketone). The inner layer may be formed by a dip coating process or by spraying a coating onto the inner surface of the intermediate layer. The low coefficient of friction of the inner layer helps to intervene the desired material through the microcatheter, so that the medicine, guide wire or other interventional systems entering the inner layer will obtain a smaller friction force to reach the lesion site in the blood vessels smoothly.

The outer surface of the outer layer of the catheter body 11 in the present embodiment is coated with a highly lubricious hydrophilic polymer. The outer layer may be made of a material with good fluidity, and the inner layer may be made of a material with poor fluidity. When the outer layer and the inner layer are hot-melt-bonded, the outer layer can penetrate and diffuse into the inner layer to achieve melting.

It should be noted that in other embodiments, the spring layer of the catheter body 11 may be a straight tube of an equal diameter, or may be a reducing tube with a diameter gradually decreasing from the proximal end to the distal end. Correspondingly, when the spring layer of the catheter body 11 is the equal-diameter straight tube, the outer layer of the catheter body 11 can either be a straight tube with a smooth outer wall of equal diameter, or an equal-diameter corrugated tube; when the spring layer of the catheter body 11 is the reducing tube that is tapered from the proximal end to the distal end, the outer layer of the catheter body 11 can be a conical tube or a conical corrugated tube of a corresponding diameter.

Figure 13:
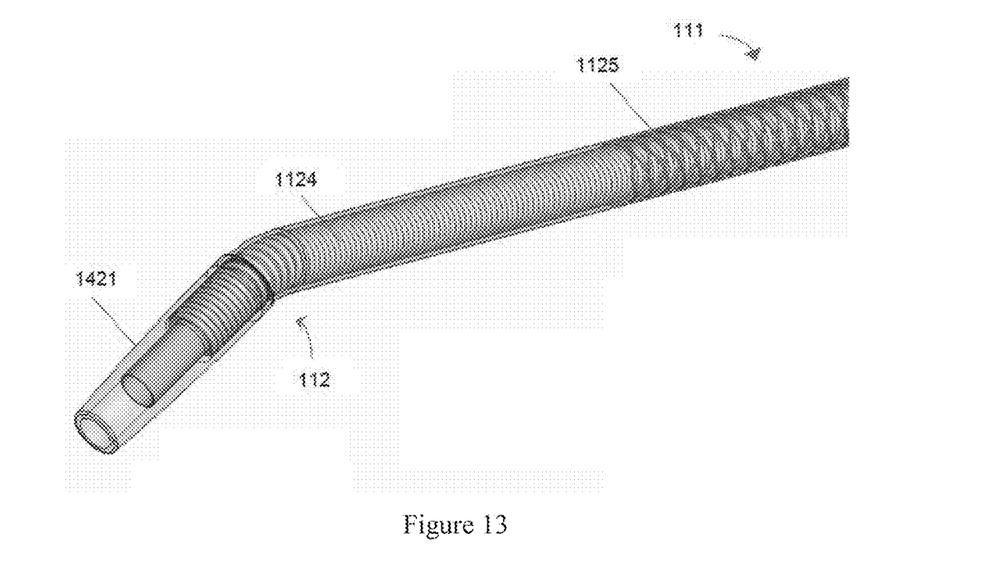
FIG. 13 is a schematic three-dimensional structure diagram of the microcatheter shown in FIG. 1.

FIG. 13 is a perspective view of the distal end of the microcatheter (shown with the outer layer being transparent), showing the shaping section 112 in a slightly curved configuration with respect to the axis of the microcatheter.

Figure 14A:
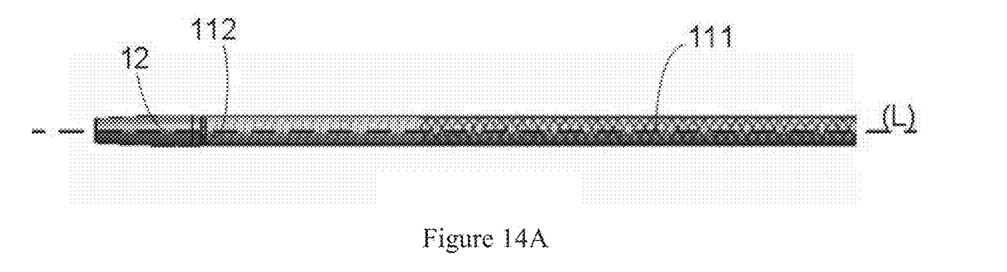
FIG. 14A is a schematic side view of a microcatheter in a first alignment position.
Figure 14B:
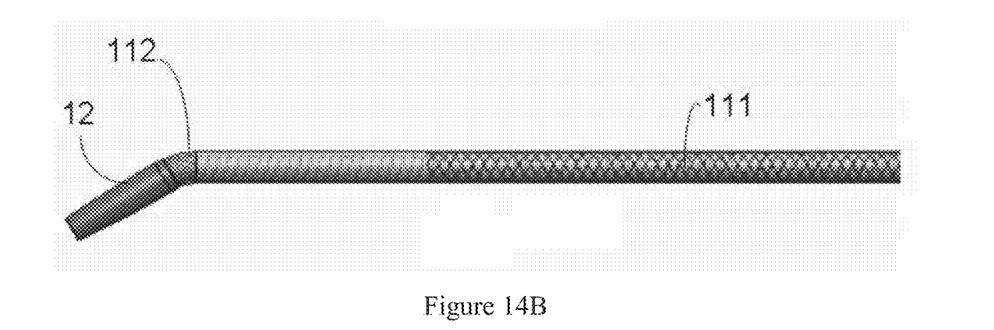
FIG. 14B is a schematic side view of a microcatheter when the shaping section begins to bend from the position shown in FIG. 14A.
Figure 14C:
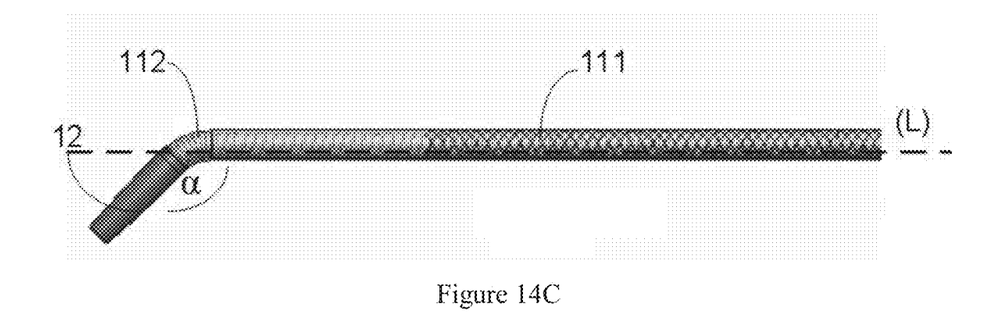
FIG. 14C is a schematic side view of a microcatheter with a sharp end bent at an angle of 45° with respect to the longitudinal axis of the microcatheter.

FIGS. 14A to 14C show a sequence in which the shaping section 112 of the microcatheter is bent from a line structure (0° with respect to the longitudinal axis L) to a bending position of about 45° with respect to the longitudinal axis L of the catheter body. Specifically, in FIG. 14A, the catheter body comprising the pushing section 111, the shaping section 112 and the sharp portion 12 is longitudinally aligned. In FIG. 14B, the shaping section 112 is being bent downward. In some embodiments, the shaping section 112 is bent downward along with the withdrawal of the guide wire, which allows the shaping section 112 to present its natural curved shape due to shape memory. As the shaping section 112 bends, the sharp portion 12 bends downward with the shaping section 112.

In FIG. 14C, the shaping section 112 reaches its stability limit based on its shape memory so that the distal end of the shaping section and the sharp portion are directed at an angle of α with respect to the axis L. In the described embodiment, the angle α is about 45°, but in various embodiments, the bending angle can be preset differently based on shape memory to manipulate the microcatheter to pass through the tortuous side branch of the vascular system. The shaping section 112 may be bent at any point of the shaping section. The angle α may range from about 25° to about 140°, about 30° to about 130°, about 40° to about 120°, about 50° to about 110°, about 30° to about 100°, about 30° to about 90°, about 50° to about 110°, about 25°, about 30°, about 40°, about 50°, about 60°, about 70°, about 80°, about 90°, about 100°, about 110°, about 120° or about 130°. Depending on the anatomy requirement of the branch entrance of a specific size, the shaping section 112 can also be directly bent into a J-shaped elbow, S-shaped or semi-circular shape. The bending point can be set by adjusting the thickness of the coil or by using the characteristics of the shape memory metal at the bending point.

Figure 15:
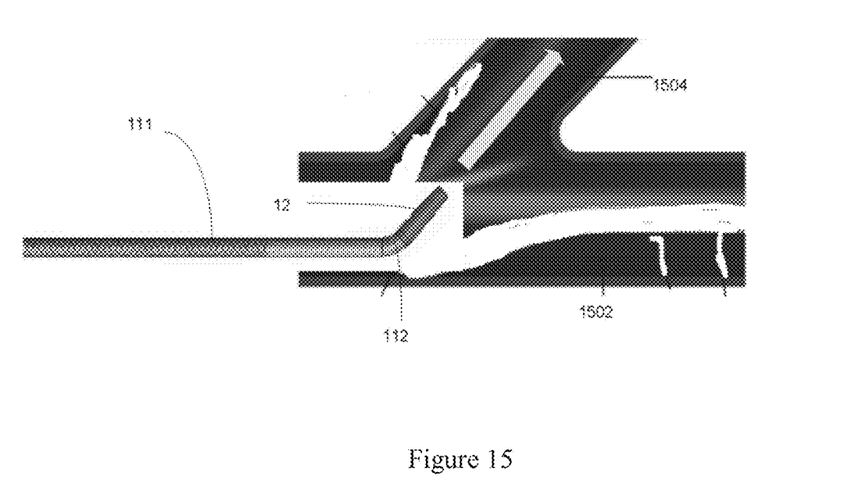
FIG. 15 is a schematic view of a side branch of the microcatheter in an access state.

FIG. 15 shows the side branch access of the microcatheter. In FIG. 15, the microcatheter is moving through the aorta 1501 in a right direction. The side branch 1502 occurs at a junction from the apex of the aorta and extends upward and rightward from the aorta. As shown in FIG. 15, the shaping section of the microcatheter 112 is bent in the way shown in FIG. 14C. In this configuration, the sharp portion 12 of the microcatheter is aligned with the side branch 1502. With proper manipulation of the microcatheter by the operator, the catheter body 11 of the microcatheter can be moved upwards and the sharp portion 12 can be guided into the side branch 1502 along the path of the arrow.

In addition, as other embodiments of the present invention, the intermediate layer 1112 of the pushing section of the catheter body 11 may also be a single-layer structure or a structure of more than three layers, but regardless of how many layers the intermediate layer 1112 of the pushing section may have, it must satisfy the requirement that the rigidity of the intermediate layer 1112 of the pushing section is greater than the rigidity of the intermediate layer 1122 of the shaping section. When the intermediate layer 1122 of the pushing section is the single-layer structure, the intermediate layer 1112 of the pushing section and the intermediate layer 1122 of the shaping section can be manufactured separately using different materials and then welded together. Alternatively, the intermediate layer 1112 of the pushing section and the intermediate layer 1122 of the shaping section are made of same material, but the material thickness or the material density of the intermediate layer 1112 of the pushing section is higher, or adopting different structures to make the rigidity of the intermediate layer 1112 of the pushing section greater than the rigidity of the intermediate layer 1122 of the shaping section.

In summary, according to the microcatheter of the present invention, the certain length range near to the sharp portion is the shaping section with prefabricating ability. This shaping section can be bent at a corresponding angle in advance in vitro to fit the angle between the branch and the main branch of the coronary artery, which allows the microcatheter to pass through the lesions in the branch smoothly; meanwhile, the pushing section can provide a certain support force and recoil force proximal to the shaping section to improve the torque control force of the microcatheter, so that the catheter body has sufficient twisting force and supporting force, thereby improving the traversing, traceability and flexibility of the microcatheter effectively.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. A microcatheter, with tubular structure, comprising a catheter body, a sharp portion disposed at a distal end of the catheter body; wherein the catheter body has a proximal end and the distal end, the catheter body comprises:
   an inner layer, with a hollow lumen;
   a tubular intermediate layer wrapped outside the inner layer, comprising a spring layer and a braid above the spring layer, the braid extending longitudinally along a part of the spring layer; and
   a tubular outer layer, wrapped outside the intermediate layer;
   wherein, a part of the spring layer which is not wrapped by the braid is bent at a certain angle along a longitudinal axis of the catheter body;
   wherein, the outer layer is a spiral corrugated tube, which comprises: a spirally convex wave crest and a concave wave trough relative to the wave crest on the outer surface of the spiral corrugated tube, and wherein the part of the spring layer which is not wrapped by the braid is a spring tube, and the wave trough of the outer layer is embedded in a gap between threads of the spring tube, the wave crest of the outer layer and the threads of the spring tube are in contact and bonded together.

2. The microcatheter of claim 1, wherein a ratio of a length of the part of the spring layer which is not wrapped by the braid to the length of the part of the spring layer which is wrapped by the braid is from 1:3 to 1:10.

3. The microcatheter of claim 1, wherein a rigidity of the intermediate layer is greater than a rigidity of the inner layer and the outer layer; the outer layer is made of a thermoplastic polymer, and the thermoplastic polymer of the outer layer is embedded in the intermediate layer so as to cover the intermediate layer.

4. The microcatheter of claim 1, wherein an outer diameter of the spring layer decreases gradually from the proximal end of the catheter body to the distal end of the catheter body.

5. The microcatheter of claim 1, wherein the braid comprises round filaments and flat filaments.

6. The microcatheter of claim 5, wherein the braid extends spirally around the spring layer in a direction of the longitudinal axis of the catheter body.

7. The microcatheter of claim 1, wherein a rigidity of the outer layer decreases gradually from the proximal end of the catheter body to the distal end of the catheter body; the outer diameter of the outer layer decreases gradually from the proximal end of the catheter body to the distal end of the catheter body; and the thickness of a wall of the outer layer decreases gradually from the proximal end of the catheter body to the distal end of the catheter body.

8. The microcatheter of claim 1, wherein the thickness of a wall of the spiral corrugated tube decreases from the proximal end to the distal end along the direction of the longitudinal axis of the catheter body, and a distance between two adjacent wave crests tends to increase from the proximal end to the distal end along the direction of the longitudinal axis of the catheter body.

9. The microcatheter of claim 1, wherein the outer diameter of the catheter body decreases gradually from 2.8 F-2.5 F to 2.1 F-1.9 F from the proximal end to the distal end, the rigidity of the catheter body transfers gradually from 120 gf-70 gf to 5 gf-2 gf from the proximal end to the distal end.

10. The microcatheter of claim 1, wherein the part of the spring layer which is not wrapped by the braid is provided at a position at a distance of 10 mm-60 mm from a tip of the sharp portion.

11. The microcatheter of claim 1, wherein the microcatheter further comprises:
   a needle base, arranged proximal to the catheter body; and
   a connecting member, located between the needle base and the catheter body, the rigidity of which is less than that of the catheter body.

12. The microcatheter of claim 1, wherein the part of the spring layer which is not wrapped by the braid is bent at a certain angle, such that the sharp portion of the distal end of the catheter body is guidable into an entrance of a side branch artery.

13. The microcatheter of claim 12, wherein the microcatheter further comprises:
- a guide wire, arranged in a lumen of the catheter body, extending through the spring layer;
- wherein by retracting the guide wire from the distal end of the spring layer, the part of the spring layer not wrapped by the braid is bent at a certain angle relative to the longitudinal axis of the catheter body, so that the sharp portion of the distal end of the catheter body is guidable into the entrance of the side branch artery.

14. The microcatheter of claim 1, wherein the portion of the spring layer which is not wrapped by the braid is bendable within a range of about 25° to about 140° with respect to the longitudinal axis of the catheter body.

* * * * *